United States Patent
Pein

(10) Patent No.: US 7,100,846 B2
(45) Date of Patent: Sep. 5, 2006

(54) WATER-JET DEVICE FOR SEPARATING A BIOLOGICAL STRUCTURE

(75) Inventor: Andreas Pein, Schwerin (DE)

(73) Assignee: Andreas Pein Medizintechnik GmbH, Schwerin (DE)

( * ) Notice: Subject to any disclaimer, the term of this patent is extended or adjusted under 35 U.S.C. 154(b) by 764 days.

(21) Appl. No.: 09/973,275

(22) Filed: Oct. 9, 2001

(65) Prior Publication Data

US 2002/0063170 A1 May 30, 2002

Related U.S. Application Data

(63) Continuation-in-part of application No. PCT/EP00/02994, filed on Apr. 4, 2000.

(30) Foreign Application Priority Data

Apr. 6, 1999 (DE) .......................... 199 15 426

(51) Int. Cl.
*B05B 01/34* (2006.01)

(52) U.S. Cl. .................. 239/483; 219/121.84; 604/23
(58) Field of Classification Search ................. 239/483, 239/486, 487, 489, 493, 498; 219/121.84, 219/121.67, 121.83; 604/23, 24, 30
See application file for complete search history.

(56) References Cited

U.S. PATENT DOCUMENTS

| 1,510,174 | A | * | 9/1924 | Kelly | ................. 239/465 |
| 5,037,431 | A | | 8/1991 | Summers | |
| 5,609,781 | A | * | 3/1997 | Kaga et al. | ........... 219/121.84 |
| 6,288,363 | B1 | * | 9/2001 | Kaga et al. | ........... 219/121.84 |

FOREIGN PATENT DOCUMENTS

| DE | 206610 C | 4/1981 |
| EP | 0551920 | 7/1993 |
| EP | 0691183 | 1/1996 |

\* cited by examiner

*Primary Examiner*—David A. Scherbel
*Assistant Examiner*—Jason Boeckmann
(74) *Attorney, Agent, or Firm*—Horst M. Kasper

(57) ABSTRACT

The water jet of a conventional water jet device is straight, bundled and impinges with its complete cross-section onto the biological structure to be separated. This renders the separating section frequently imprecise and requires an increased flow pressure. Therefore, a water jet device with a novel separating nozzle (14) is furnished. This separating nozzle (14) is furnished with a nozzle channel (15), wherein the nozzle channel (15) is furnished with one or several twisted grooves (16) at the circumference of the nozzle channel (15) and wherein the number of the twisted grooves (16) and the diameter and the length of the nozzle channel (15) are placed in such ratio that the separating jet subjected to pressure is rotated.

48 Claims, 3 Drawing Sheets

WATER-JET DEVICE FOR SEPARATING A BIOLOGICAL STRUCTURE

CROSS REFERENCE TO RELATED APPLICATIONS

This application is a continuation-in-part application of another international application filed under the Patent Cooperation treaty on Apr. 4, 2000 bearing Application No. PCT/EP00/02994, and listing the United States as a designed and/or elected country. The entire disclosure of this latter application, including the drawings thereof, is hereby incorporated in this application as if fully set forth herein.

BACKGROUND OF THE INVENTION

1. Field of the Invention

The Invention relates to a water jet device for separating a biological structure.

2. Brief Description of the Background of the Invention Including Prior Art

Water jet devices and their application in the medical field are known in many variations. The advantage of water jet devices relative to mechanical surgical devices and methods is based first in a more gentle treatment of the biological structures.

In general such devices are associated with the disadvantage that the separating liquid cannot be maintained sterile and that the pressure of the separating medium exiting is subject to relatively large variations.

Now a water jet device is described in the German printed patent document DE 4200976, which avoids these disadvantages and which comprises essentially a pressure loaded piston cylinder device, wherein a receiver container for the separating medium is fitted into the cylinder space of the piston cylinder device. The receiver container for the separating medium is here a cartridge and is connected to a separating nozzle through a line. The separating medium is kept sterile by the separation of pressure medium and separating medium and by the stable cartridge and the pressure situations of the separating medium remain constant and reproducible.

This assures a water jet in a laminar region and thereby an advantageous sharp edge feature of the water jet.

A similar water jet device is known from the U.S. Pat. No. 5,037,431, wherein the water jet device is also furnished with a separating nozzle, wherein the separating nozzle is disposed at the distal end of the supply line and exhibits a circular cross-section.

All water jet devices known up to now are however associated with the disadvantage that the water jet impinges onto the biological structure bundled and with its total cross-section. For example soft tissue easily yields to this pressure such that a relatively wide and also frequently dirty separating cut results. The biological structure is thereby exerted and loaded excessively. A further refinement of the water jet by a further reduction of the nozzle diameter is technically limited. Such a water jet is also difficult to apply under liquid, since such water jet exhibits disintegration appearances already shortly after the exiting out of the nozzle and since the separating sharpness of the water jet is lost. In particular cases an increased destruction of the biological structure is associated with a necessary increase of the flow pressure, since in addition the separating force of the water jet is determined exclusively by the size of the flow pressure freely selectable by the operator.

SUMMARY OF THE INVENTION

1. Purposes of the Invention

It is an object of the present invention to improve the separating sharpness of water jet devices of the preceding kind and to maintain water jet devices as far as possible independent of the flow pressure of the separating medium.

These and other objects and advantages of the present invention will become evident from the description which follows.

2. Brief Description of the Invention

The present invention provides a water jet device for separating of a biological structure. The water jet includes a pressure flow generator, an operatable control and automatic control unit and a supply capillary with a separating nozzle. The separating jet exits from the separating nozzle. The separating nozzle is furnished with the nozzle channel with a cylindrical section and the separating nozzle is disposed at the distal end of the supply capillary. The separating nozzle is disposed fixedly positioned and coaxial to the supply capillary. The nozzle channel is furnished with at least one twisted groove. The number of the twisted grooves and the diameter and the length of the nozzle channel are placed in such a ratio to each other that the separating jet subjected to pressure is rotated.

The slope of the spiral flutes is preferably dimensioned larger than the diameter of the nozzle channel. The spiral flutes can exhibit a rounded cross-sectional shape. The supply capillary is preferably equipped with one or several additional separating tools for mechanical working of the biological structure in the region of the separating nozzle of the supply capillary. The supply capillary is preferably made out of a current conducting material and is advantageously connectable to a high frequency current supply device.

The present invention eliminates the recited disadvantages of the state of the art.

The high separating accuracy of the water jet is a particular advantage. The separating precision is further increased by the novel and rotated water jet relative to a laminar and straight directed water jet. This is achieved by having the water particles transposed into the outer circumference of the water jet by the rotation of the water jet, where the water particles assume an increased circumferential speed relative to the water particles remaining in the middle and thus form a cutting-edge circulating in the circumferential region. This circulating cutting-edge is comparable with the circulating blade of a wood drill or of a hole circular saw and separates more precisely as the complete attack face of a straight water jet because of the smaller attack face of the separating edge. The liquid pressure can be decreased with the improved separating effect, which is associated with advantageous effects energetically for the complete water jet device. The water jet formed in this manner does not only drill very well into the most different biological structures, but also into liquids. Therefore the new water jet is also extremely suitable for operations under liquids because of the maintenance of coherence by the water jet.

It is also advantageous that the lesser axial force component of the flow pressure also generates a lesser counter force observable as recoil. This alleviates the operation since the operator does not have to observe the distance of the separating nozzle from the tissue. In contrast the feeling for the momentary separating force remains with the operator without disadvantageous effects, since the momentary flow force is made felt to the operator by the counter force of the radial force component acting on the handle. This all increases the capability of the operator to concentrate. The new rotated water jet forms with extremely sharp edges by the relationship of diameter and length of the nozzle channel. It is also very advantageous for the sharp edge feature of the water jet, if for this purpose a slope of the spiral flutes is selected, wherein the slope of the spiral flutes is larger than the diameter of the nozzle channel. It is also an advantage for the formation of a sharp edge water jet, if a rounded cross-sectional shape is selected for the spiral flutes.

It has proven to be advantageous where the supply capillary is employed supporting that the water jet as a blunt separating tool, which as far as possible makes a sharp preparation of the tissue unnecessary and thereby avoids stronger bleedings. The new supply capillary can also be combined with other mechanical separating tools. This expands the field of application of the water jet device.

It is a particular advantage where the supply capillary is made of a current conducting material and is connectable to a high frequency mono polar or bipolar current supply device. For example such thin tissue threads can thereby be separated by heat in an expansion space between different tissue structures, where such thin tissue structures would escape from a water jet.

The invention is to be explained in more detail in the following by way of an example embodiment.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing, in which are shown several of the various possible embodiments of the present invention.

DESCRIPTION OF INVENTION AND PREFERRED EMBODIMENT

Figure 1:
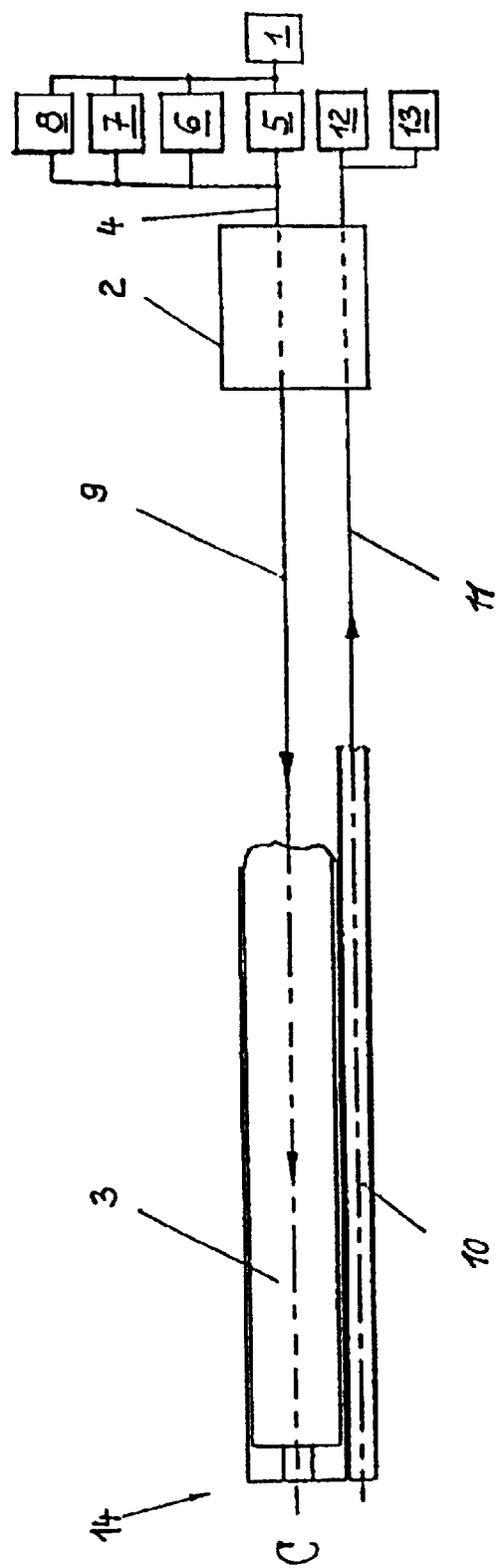
FIG. 1: a simplified and symbolic view of a water jet device.

The water jet device comprises mainly according to FIG. 1 a pressure stream generator 1, a control and automatic control unit 2 and a supply capillary 3 with a handle. A connectable pulse generator 5 is switched in between the pressure line 4 leading from the pressure current generator 1 to the control and automatic control unit 2, wherein further additional devices such as for example a laser device 6, a heating device 7 and/or a freezing device 8 are switched in parallel to the pulse generator 5. The control and automatic control unit 2 is furnished with a supply capillary 3 and is furnished with actuating devices not illustrated, wherein the operator can preselect all parameters influencing the water jet with the aid of the actuating devices and can steplessly and automatically control all the parameters. The control and automatic control device 2 is connected to a supply capillary 3 through a supply line 9. A discharge capillary 10 can be furnished disposed parallel to the supply capillary 3, wherein the discharge capillary 10 can be furnished in a constructive unit or as a separate element with respect to the supply capillary 3 and wherein the discharge capillary 10 is connected to the control and automatic control unit 2 through a discharge line 11. An automatically controllable discharge pump 12 supplies the required under-pressure. One or several controllable and automatically controllable additional units 13 are disposed in parallel to the discharge pump 12.

Figure 2:
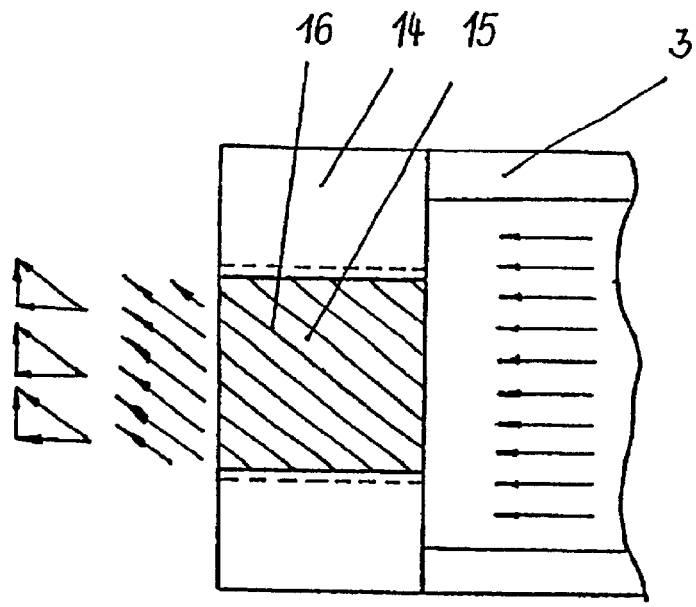
FIG. 2: a precision nozzle in a partial sectional view.
Figure 3:
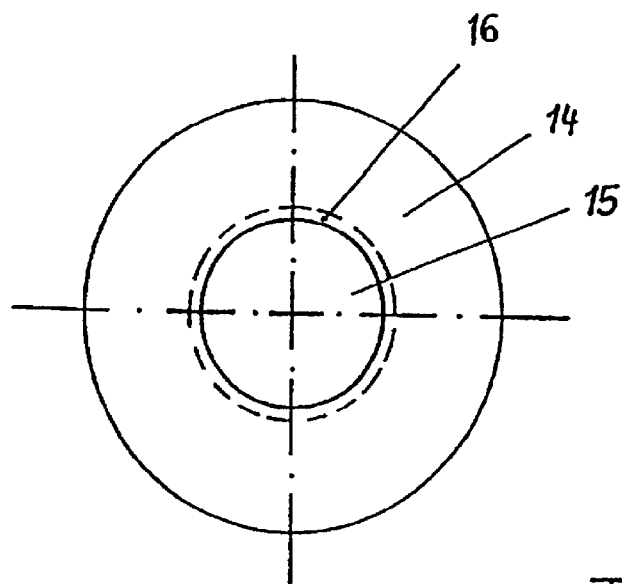
FIG. 3: the precision nozzle in a front elevational view.

The supply capillary 3 is furnished at its distal end with the separating nozzle 14 according to the present invention as shown in FIGS. 2 and 3. This separating nozzle 14 is furnished with a nozzle channel 15, wherein the nozzle channel 15 is in a particular way equipped with the one or several parallel and circulating twisted grooves or spiral flutes 16. The spiral grooves 16 can exhibit an arbitrary cross-sectional shape, wherein a round cross-sectional shape is advantageous. The ratio of the slope of the spiral flutes 16 to the diameter of the nozzle channel 15 is selected larger than 1 from a flow technical point of view.

The supply capillary 3 is constructed such in connection with the separating nozzle 14 that the distal end of the supply capillary 3 is employable as an additional mechanically acting separating agent.

Figure 4:
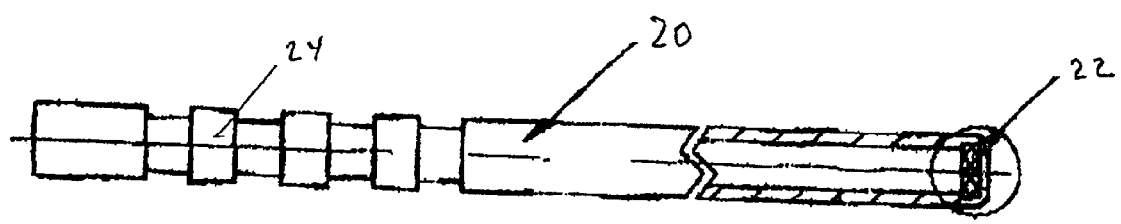
FIG. 4 a side elevational and in part sectional view of a capillary with inserted nozzle stone, FIG. 5 a sectional and in part side elevational view of the nozzle stone with a spiral groove.

FIG. 4 shows a capillary 20 with inserted nozzle stone 22. The capillary 20 provides that a laminar flow of water is generated and passes into the nozzle stone 22. A handle 24 with a contour suitable for gripping supports the capillary 20.

Figure 5:
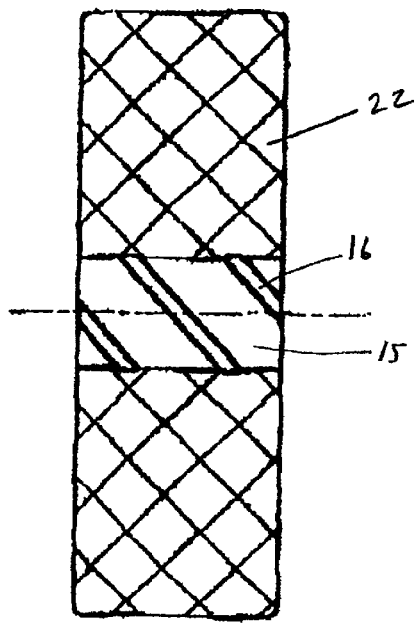

FIG. 5 shows the nozzle stone 22. The nozzle stone is formed as a ring adapted to be fitted into the capillary 20 with an outer cylinder surface. A inner cylindrical surface of the nozzle stone is furnished with spiral grooves 16. The repetition rate of the spirals can be from about 1 to 5 times the diameter of the inner cylinder and is preferably from about 1.5 to 3 times the inner of the inner cylinder of the nozzle stone 22. The diameter of the inner cylinder can be from about 0.2 to 10 millimeters and is preferably from about 0.5 to 3 millimeters. The length of the inner cylinder can be from about 1 to 5 times the diameter of the inner cylinder and is preferably from about 1.5 to 3 times the diameter of the inner cylinder. The length of the capillary 20 can be from about 10 to 50 times the length of the nozzle stone and is preferably from about 15 to 30 times the length of the nozzle stone 22. The length of the capillary can be from about 0.5 to 2 times the length of the handle section of the water jet generator.

The width of the spiral grooves can be from about 0.05 to 0.4 times the diameter of the inner cylinder of the nozzle stone 22 and is preferably 0.08 to 0.2 times the diameter of the inner cylinder of the nozzle stone 22. The depth of the spiral grooves can be from about 0.1 to 1 times the width of the spiral grooves and is preferably 0.2 to 0.4 times the width of the spiral grooves.

The mode of operation of the water jet device is to be described by way of the hydro disectional method. Initially the water jet device is here made ready for operation such that the water jet is available with a correspondingly preprogrammed pressure, quantity and temperature ready for calling. Then the supply capillary 3 is inserted, punctured and pierced into the tissue and is led into the boundary layer region of different tissues. Liquid is applied in this region in the following through the supply capillary 3, whereby an expansion space forms between the different tissues and wherein the expansion space presses the tissues apart from each other. Soft tissue components are here already dissected at the lowest pressures, hard or elastic structures are tensioned and remain initially still uninjured. In case of very firmly at each other resting structures, this process can be supported by a pulsating the water jet.

The water jet exhibits here a particular effect. The laminar flow of the water jet is deflected by the spiral grooves 16 disposed in the nozzle channel 15 of the separating nozzle 14 and a rotary motion is initiated in circumferential direction. The flow force of the water jet directed into the separating nozzle 14 is thereby subdivided into an axial remaining force component and a radially added force component. Preferably, a rotary force or a tangential force is present in the emitted water jet. A rotated water jet is formed, where the laminar flow remains in the water jet since the tracks of motion of the individual water particles remain running further parallel to each other. The radially acting force component interacts with the water jet and transposes increasingly into the region close to the circumference, where the water particles move with an increased circumferential speed. A closed circulating separating edge in a form comparable to a wood drill is thereby formed in this region of the water jet. Of course this separating edge of the water jet exhibits naturally an increased separating force relative to a straight water jet.

The rotating water jet will not disintegrate or lose its rotation after exiting from the nozzle stone 22. A rotating water jet receives sufficient linear and rotary energy to prevail against air resistance outside of the nozzle stone 22 and to further deliver the cutting action in the biological structure. The water jet is furnished with the necessary energy for accomplishing this from the water pressure ahead of the nozzle stone 22 and by the geometric conditions of the nozzle stone 22 and of the nozzle channel 15. The water amount entered through the supply capillary 3 can be withdrawn again from the tissue region through the discharge capillary 10 if required.

It will be understood that each of the elements described above, or two or more together, may also find a useful application in other types of water jet system configurations and tissue processing procedures differing from the types described above.

While the invention has been illustrated and described as embodied in the context of a water jet device for separating of a biological structure, it is not intended to be limited to the details shown, since various modifications and structural changes may be made without departing in any way from the spirit of the present invention.

Without further analysis, the foregoing will so fully reveal the gist of is the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A water jet device for separating of a biological structure, essentially comprising a pressure water flow generator (1), an operatable control and automatic water control unit (2) and a supply capillary (3) with a separating nozzle (14), wherein a separating water jet exits from the separating nozzle (14), wherein the separating nozzle (14) is furnished with a nozzle channel (15) with a circular cross-section and wherein the separating nozzle (14) is disposed at the distal end of the supply capillary (3), wherein the separating nozzle (14), is disposed fixedly positioned and coaxial to the supply capillary (3) and wherein the nozzle channel (15) is furnished with at least one spiral groove (16) and wherein the number of the spiral grooves (16) and the diameter and the length of the nozzle channel (15) are placed in such a ratio to each other that the separating water jet subjected to pressure is rotated.

2. The water jet device according to claim 1 wherein the nozzle channel (15) is a hollow cylinder, wherein a slope of the spiral grooves (16) is dimensioned larger than the diameter of the nozzle channel (15) and wherein the spiral grooves are recessed into the hollow cylinder and exhibit a slope angle of from about 30 to 45 degrees.

3. The water jet device according to claim 2 wherein the spiral grooves (16) exhibit a rounded cross-sectional shape.

4. The water jet device according to claim 1 wherein the supply capillary (3) is equipped with one or several additional separating tools for mechanical working of the biological structure in the region of the separating nozzle (14) of the supply capillary (3).

5. The water jet device according to claim 1 wherein the supply capillary (3) is made out of a current conducting material and is connectable to a high frequency current supply device.

6. A water jet device for separating of a biological structure comprising a pressure water flow generator;
an operatable control and automatic water control unit;
a supply capillary connected to the pressure water flow generator;
a separating nozzle attached to the supply capillary and wherein the separating nozzle is disposed at the distal end of the supply capillary, wherein the separating nozzle is disposed fixedly positioned and coaxial at the supply capillary,
wherein the separating nozzle is furnished with a nozzle channel for forming a water jet to exit from the separating nozzle;
at least one spiral groove furnished in the nozzle channel and wherein the spiral groove and the diameter and the length of the nozzle channel are placed in such a ratio to each other that the flowing stream of water in the nozzle channel subjected to pressure is rotated and a rotating water jet is released by the nozzle channel.

7. The water jet device according to claim 6 wherein the nozzle channel is formed as a hollow cylinder, wherein a slope of the spiral groove is dimensioned larger than the diameter of the nozzle channel and wherein the spiral groove exhibits a slope angle of from about 30 to 45 degrees.

8. The water jet device according to claim 7 wherein the spiral groove is recessed into the hollow cylinder of the nozzle channel, wherein the spiral groove exhibits a rounded cross-sectional shape.

9. The water jet device according to claim 6 wherein the supply capillary is equipped with one or several additional separating tools for mechanical working of the biological structure in the region of the separating nozzle of the supply capillary.

10. The water jet device according to claim 6 wherein the supply capillary is made out of a current conducting material and is connectable to a high frequency current supply device.

11. The water jet device according to claim 6 wherein the nozzle channel has a circular cross-section modified by the cross-section of the spiral groove.

12. The water jet device according to claim 6 further comprising
a second spiral groove disposed running parallel to the first spiral groove in the nozzle channel.

13. The water jet device according to claim 6 wherein the separating nozzle has an overall shape of a hollow cylinder and wherein the nozzle channel has a shape of a hollow cylinder bore modified by the placing of the spiral groove.

14. A water jet device for separating of a biological structure, essentially comprising a pressure water flow generator (1), an operatable control and automatic water control unit (2) and a supply capillary (3) with a separating nozzle (14),
wherein an axis of the separating nozzle (14) coincides in direction with an adjacently disposed axis of the supply capillary (3),
wherein the separating water jet exits from the separating nozzle (14),
wherein the separating nozzle (14) is furnished with a nozzle channel (15) with a circular cross-section and wherein the separating nozzle (14) is disposed at a distal end of the supply capillary (3),
wherein the separating nozzle (14) is disposed fixedly positioned and coaxial to the supply capillary (3) and wherein the nozzle channel (15) is furnished with at least one twisted groove (16) and wherein the number of the twisted grooves (16) and the diameter and the length of the nozzle channel (15) are placed in such a ratio to each other that the separating jet subjected to pressure is rotated.

15. A water jet device for separating of a biological structure comprising
a pressure flow generator;
an operatable control and automatic control unit;
a supply capillary connected to the pressure flow generator;
a separating nozzle attached to the supply capillary and wherein the separating nozzle is disposed at a distal end of the supply capillary, wherein the separating nozzle is disposed fixedly positioned and coaxial at the supply capillary,
wherein the separating nozzle is furnished with a nozzle channel for forming a water jet to exit from the separating nozzle;
at least one spiral groove furnished in the nozzle channel and wherein the spiral groove and the diameter and the length of the nozzle channel are placed in such a ratio to each other that the flowing stream of water in the nozzle channel subjected to pressure is rotated and a rotating water jet is released by the nozzle channel;
a pressure line leading from the pressure flow generator to the operatable control and automatic control unit;
a connectable pulse generator placed into the pressure line.

16. The water jet device according to claim 15 further comprising
a laser device switched in parallel to the pulse generator.

17. The water jet device according to claim 15 further comprising
a heating device switched in parallel to the pulse generator.

18. The water jet device according to claim 15 further comprising
a freezing device switched in parallel to the pulse generator.

19. The water jet device according to claim 15 further comprising
a discharge capillary disposed parallel to the supply capillary and connected to the operatable control and automatic control unit through a discharge line; an automatically controllable discharge pump connected to the discharge line.

20. The water jet device according to claim 13 wherein the hollow cylinder has a length of an inner cylinder which is from about 1 to 5 times the diameter of the inner cylinder;
wherein the inner cylinder is furnished with spiral grooves;
wherein the width of the spiral grooves is 0.08 to 0.2 times the diameter of the inner cylinder of the nozzle;
wherein the depth of the spiral grooves is 0.2 to 0.4 times the width of the spiral grooves.

21. A. method for separating biological structures comprising the steps of:
furnishing a water jet device including a pressure flow generator, an operatable control and automatic control unit, a supply capillary connected to the pressure flow generator, a separating nozzle attached to the supply capillary and wherein the separating nozzle is disposed at the distal end of the supply capillary, wherein the separating nozzle is disposed fixedly positioned and coaxial at the supply capillary;
making the water jet ready for operation such that the water jet is available with a correspondingly pre-programmed pressure, quantity and temperature ready for calling;
inserting, puncturing and piercing the supply capillary into the tissue;
leading the supply capillary into a boundary layer region of different tissues;
applying liquid in this boundary layer region in the following through the supply capillary;
forming an expansion space between different tissues; and pressing tissues apart from each other with the expansion space.

22. The method for separating biological structures according to claim 21 further comprising the steps of:
dissecting soft tissue components here already at the lowest pressures;
tensioning bard or elastic structures while remaining initially still uninjured.

23. The method for separating biological structures according to claim 21 further comprising the steps of:
supporting a dissecting process by a pulsating water jet in case of very firmly at each other resting structures.

24. The method for separating biological structures according to claim 21 further comprising the steps of:
deflecting a laminar flow of the water jet by spiral grooves disposed in a nozzle channel of the separating nozzle;
initiating a rotary motion in circumferential direction of the water;
directing a flow force of the water jet into the separating nozzle to be thereby subdivided into an axial remaining force component and a radially added force component;
forming a rotated water jet, where the laminar flow remains in the water jet since the tracks of motion of the individual water particles remain running further parallel to each other.

25. The method for separating biological structures according to claim 24 further comprising the steps of:
   interacting a radially acting force component with the water jet and transposing the water jet increasingly into a region close to the circumference, where the water particles move with an increased circumferential speed;
   forming a closed circulating separating edge in a form comparable to a wood drill in this region of the water jet, wherein this separating edge exhibits naturally an increased separating force relative to a straight water jet.

26. The method for separating biological structures according to claim 21 further comprising the steps of:
   withdrawing a water amount entered through the supply capillary again from the tissue region through the discharge capillary if desired.

27. The water jet device according to claim 1 further comprising
   a pressure line leading from the pressure water flow generator to the operatable control and automatic water control unit; a connectable water pulse generator placed into the pressure line.

28. A water jet device for separating of a biological structure comprising
   a pressure water flow generator for water;
   an operatable control and automatic water control unit;
   a supply capillary connected to the pressure water flow generator for supporting a flow of the water from the pressure water flow generator;
   a separating nozzle attached to the supply capillary and wherein the separating nozzle is disposed at a distal end of the supply capillary, wherein the separating nozzle is disposed fixedly positioned and coaxial at the supply capillary for guiding water coming from the supply capillary,
   wherein the separating nozzle is furnished with a nozzle channel for forming a water jet to exit from the separating nozzle;
   at least one spiral groove furnished in the nozzle channel and wherein the spiral groove and the diameter and the length of the nozzle channel are placed in such a ratio to each other that the flowing stream of water in the nozzle channel subjected to pressure is rotated and a rotating water jet is released by the nozzle channel.

29. A water jet device for separating of a biological structure comprising
   a pressure water flow generator;
   an operatable control and automatic water control unit;
   a supply capillary connected to the pressure water flow generator;
   a separating nozzle attached to the supply capillary and wherein the separating nozzle is disposed at the distal end of the supply capillary,
   wherein the separating nozzle is disposed fixedly positioned and coaxial at the supply capillary,
   wherein the separating nozzle is furnished with a nozzle channel for forming a water jet to exit from the separating nozzle.

30. The water jet device according to claim 29 wherein the separating nozzle comprises a nozzle stone (22) inserted into the supply capillary, wherein the nozzle stone (22) is formed as a ring adapted to be fitted into the supply capillary with an outer cylinder surface wherein the supply capillary provides that a laminar flow of water is generated and passes into the nozzle stone (22), wherein a handle (24) with a contour suitable for gripping supports the supply capillary, wherein an inner cylindrical surface of the nozzle stone is furnished with spiral grooves (16), wherein the rotating water jet remains integrated after exiting from the nozzle stone (22), wherein the rotating water jet receives sufficient linear and rotary energy to prevail against air resistance outside of the nozzle stone (22) and to further deliver the cutting action in the biological structure.

31. The water jet device according to claim 29 further comprising
   a pressure line leading from the pressure water flow generator to the operatable control and automatic water control unit;
   a connectable water pulse generator placed into the pressure line.

32. The water jet device according to claim 31 further comprising
   a laser device switched in parallel to the water pulse generator.

33. (previously presented) The water jet device according to claim 31 further comprising
   a heating device switched in parallel to the water pulse generator.

34. The water jet device according to claim 31 further comprising
   a freezing device switched in parallel to the water pulse generator.

35. The water jet device according to claim 29 further comprising
   a discharge capillary disposed parallel to the supply capillary and connected to the operatable control and automatic water control unit through a discharge line;
   an automatically controllable water discharge pump connected to the discharge line.

36. The water jet device according to claim 29 wherein the separating nozzle is unprotected and unshielded for immediate engagement with the biological structure to be separated.

37. The water jet device according to claim 29 wherein the separating nozzle is protruding from the supply capillary as a separate projection.

38. The water jet device according to claim 29 wherein the separating nozzle has a blank front end not protected by other structures for furnishing a separating water jet having a laminar flow of water and wherein the blank front end furnishes uninhibited engagement of the separating nozzle with the biological structure,
   protruding from the supply capillary as a separate projection.

39. The water jet device according to claim 29 wherein the nozzle channel is formed as a hollow cylinder and wherein the hollow cylinder extends up to a discharge end of the separating nozzle.

40. The water jet device according to claim 29 further comprising
   a discharge capillary disposed parallel to the supply capillary and connected to the operatable control and automatic water control unit through a discharge line, wherein the separating nozzle and an open end of the discharge capillary are disposed neighboring in a common projecting structure for an immediate engagement with a biological structure;
   an automatically controllable water discharge pump connected to the discharge line.

41. The water jet device according to claim 29 further comprising water disposed in the supply capillary and in the separating nozzle.

42. The water jet device according to claim 29 wherein only a single separating nozzle with a single nozzle channel is present.

43. The water jet device according to claim 29 wherein the separating nozzle essentially consists of a single nozzle channel.

44. The water jet device according to claim 43 further comprising a spiral groove disposed in the single nozzle channel for generating a stable rotating water-jet.

45. The water jet device according to claim 29 wherein the nozzle channel is adapted to eject a stable stream of water.

46. The water jet device according to claim 45 wherein an exit end of the nozzle channel has an inner cylindrical shape with an inner spiral groove for ejecting a rotating aqueous jet with a round cross-section.

47. The water jet device according to claim 29 wherein the nozzle channel is constructed for an essentially incompressible aqueous liquid to be formed as a stable aqueous jet.

48. The water jet device according to claim 47 wherein an exit end of the nozzle channel has a cylindrical shape for ejecting the stable aqueous jet with a round cross-section.

* * * * *